United States Patent

Auguste et al.

[11] Patent Number: 6,051,748
[45] Date of Patent: Apr. 18, 2000

[54] HYDROPHILE ADHESIVE MASS

[75] Inventors: Stéphane Auguste, Quetigny; Laurent Apert, Dijon, both of France

[73] Assignee: Laboratoires d'Hygiene et de Dietetique, Paris, France

[21] Appl. No.: 09/068,545

[22] PCT Filed: Sep. 15, 1997

[86] PCT No.: PCT/FR97/01621

§ 371 Date: May 15, 1998

§ 102(e) Date: May 15, 1998

[87] PCT Pub. No.: WO98/10801

PCT Pub. Date: Mar. 19, 1998

[30] Foreign Application Priority Data

Sep. 16, 1996 [FR] France ................................. 96 11249

[51] Int. Cl.⁷ ..................................................... A61F 13/00
[52] U.S. Cl. ............................. 602/54; 602/48; 428/355; 424/443; 128/156
[58] Field of Search ........................ 602/48, 54; 424/443; 428/355; 128/156

[56] References Cited

U.S. PATENT DOCUMENTS 4,367,732   1/1983   Poulsen et al. .
4,393,080   7/1983   Pawelchak et al. .
5,827,528  10/1998   Kubo et al. .

Primary Examiner—John G. Weiss
Assistant Examiner—Kelvin Hart
Attorney, Agent, or Firm—Dennison, Scheiner, Schultz & Wakeman

[57] ABSTRACT

The invention concerns a novel hydrophile adhesive mass to be used for medical purposes characterised in that said hydrophile adhesive mass comprises:

(a) 10 to 35 parts by weight of sequenced poly(styrene/olefin/styrene) copolymer, in particular poly(styrene/isoprene/styrene), (b) 20 to 50 parts by weight of a tackifier resin, (c) 2 to 15 parts by weight of an acrylate polymer with a glass temperature less than −20° C., (d) 2 to 25 parts by weight of a plasticizer, in particular a plasticizing oil, (e) 20 to 50 parts by weight of a hydrocolloid, (f) 0.1 to 2 parts by weight of at least one antioxidant.

The invention also concerns the use of this adhesive mass for making protective bandages, in particular for treating blisters, skin-deep dermo-epidermic lesions, exudative wounds and burns.

25 Claims, No Drawings

HYDROPHILE ADHESIVE MASS

FIELD OF THE INVENTION

The present invention relates to novel hydrophilic adhesive masses based on a block copolymer of the poly(styrene/olefin/styrene) type and on a hydrocolloid, with which an acrylate polymer is associated for increasing the absorption capacity of the hydrocolloid. The invention further relates to the use of these novel adhesive masses for medical purposes, in particular for the production of protective dressings and especially anti-blister dressings and dressings for the treatment of superficial dermo-epidermal lesions, exudative wounds and burns.

PRIOR ART

Numerous hydrophilic adhesive masses employed in these various medical applications have already been described. Examples which may thus be mentioned are patent applications FR-A-2,495,473, EP-A-130,061, EP-A-092,999 and EP-A-302,536 and U.S. Pat. No. 3,972,328.

The hydrophilic adhesive masses described in these documents are formed principally of an adhesive elastomer selected from polymers such as polyisobutenes or poly(styrene/olefin/styrene) block copolymers, for example poly(styrene/isoprene/styrene) or poly(styrene/ethylene/butylene/styrene), which may or may not be associated with so-called "tackifying" resins, plasticizers etc., and of one or more hydrocolloids.

The adhesive elastomer of a hydrophobic nature makes it possible to give the mass properties of elasticity, deformation or shock absorption (for example in an anti-blister dressing) but also of cohesion sufficient to prevent the adhesive from flowing out of the mass and allow ease of handling. However, it is incapable of absorbing liquids, so the resulting products do not easily stick to wet skin and do not stick, or quickly become unstuck, as soon as perspiration or exudates are absorbed.

By virtue of its hydrophilic character, the hydrocolloid gives these adhesive masses their properties of absorbing water, perspiration, liquids or exudates. However, it then has a tendency to swell, causing a loss of cohesion and meaning that the dressing comes apart when removed or is even lost.

Associating the properties of the adhesive elastomer with those of the hydrocolloid does not suffice to satisfy the numerous and often contradictory demands which are made on such hydrophilic adhesive masses in the context of the above-mentioned medical applications. Furthermore, given that it is also necessary to take account of the possible combinations of the compounds making up the formulation of the mass, there is very little room to manoeuvre in the production, for medical purposes, of a hydrophilic adhesive mass which has a maximum absorption and a durable adhesion over time. Finally, these products are additionally subject to more specific constraints; for example, they have to stick to the skin but not to the wound, protect the wound but avoid the problems of irritation and maceration, etc.

The various formulations and the various specific additives for improving the efficacy of the adhesive elastomer/hydrocolloid couple proposed in the documents cited above illustrate the need for and the difficulty of optimising the absorption properties without detracting from the adhesion properties and while at the same time taking into account all the above-mentioned demands for obtaining more efficient products and widening the formulation possibilities.

However, none of the publications referred to above discloses or suggests the novel specific hydrophilic adhesive masses of the invention, which provide a novel, efficient and unexpected solution, in terms of both absorption and adhesion, to the demands and problems presented by the production of hydrophilic adhesive masses for medical purposes.

OBJECTS OF THE INVENTION

In the field of hydrophilic adhesive masses employed for medical purposes, it would therefore be desirable to find a novel technical solution making it possible to achieve a compromise between the above-mentioned demands.

According to a first aspect of the invention, it is proposed to provide a novel hydrophilic adhesive mass wherein an acrylate polymer is added to a hydrocolloid and a styrene/olefin/styrene block copolymer, especially a poly(styrene/isoprene/styrene).

According to a second aspect of the invention, it is proposed to use this novel hydrophilic adhesive mass for the production of protective dressings and especially dressings for the treatment of blisters and for the treatment of superficial dermo-epidermal lesions, exudative wounds and burns.

SUBJECT OF THE INVENTION

The above-mentioned objects are achieved by virtue of a novel technical solution consisting in the production of a hydrophilic adhesive mass which can be used for medical purposes, characterised in that said hydrophilic adhesive mass comprises:

(a) 10 to 35 parts by weight of a styrene/olefin/styrene block copolymer, especially a poly(styrene/isoprene/styrene), (b) 20 to 50 parts by weight of a tackifying resin, (c) 2 to 15 parts by weight of an acrylate polymer with a glass transition temperature below $-20°$ C., (d) 2 to 25 parts by weight of a plasticizer, especially a plasticizing oil, (e) 20 to 50 parts by weight of a hydrocolloid, and (f) 0.1 to 2 parts by weight of at least one antioxidant.

According to one currently preferred embodiment, this hydrophilic adhesive mass comprises, for a total of 100 parts by weight:

18 to 22 and preferably 19.8 parts by weight of a poly(styrene/isoprene/styrene) three-block copolymer, 25 to 35 and preferably 30.2 parts by weight of a tackifying resin, 3 to 8 and preferably 4.9 parts by weight of an n-butyl acrylate/acrylic acid copolymer with a glass transition temperature of $-39°$ C., 10 to 20 and preferably 14.3 parts by weight of a mineral plasticizing oil, 25 to 35 and preferably 30 parts by weight of sodium carboxymethyl cellulose, 0.3 to 0.8 and preferably 0.4 part by weight of a phenolic antioxidant, and 0.3 to 0.8 and preferably 0.4 part by weight of the sulphur-containing antioxidant zinc dibutyldithiocarbamate.

It is recommended to use the hydrophilic adhesive mass for the production of protective dressings, particularly for the treatment of blisters, superficial dermo- epidermal lesions of the skin, exudative wounds and burns.

The block copolymers of the styrene/olefin/styrene type which can be used within the framework of the present invention are the ones normally used by those skilled in the art in the preparation of adhesive mass, and reference may be made in this connection to the above-mentioned document of the state of the art.

The olefin blocks of these copolymers can consist of isoprene, butadiene or ethylene/butylene units.

Among these, poly(styrene/isoprene/styrene) three-block copolymers are preferred.

Poly(styrene/isoprene/styrene) three-block copolymer [abbreviated to poly(SIS)] is understood here as meaning a poly(SIS) material with a styrene content of between 14 and 52% by weight, based on the weight of said poly(SIS). This expression also covers poly(SIS) materials containing a mixture of poly(SIS) three-block copolymers and two-block copolymers of the poly(styrene/isoprene) type.

Such products, which are well known to those skilled in the art, are marketed for example by SHELL and EXXON CHEMICAL under the names KRATON® D and VECTOR®, respectively.

Within the framework of the present invention, three-block copolymers with a styrene content of between 14 and 30% by weight, based on the weight of said poly(SIS), are preferred. The products marketed by EXXON CHEMICAL and SHELL CHEMICALS under the names VECTOR® 4114 and KRATON® D-1111CS, respectively, will be particularly preferred.

Among the tackifying resins which are suitable according to the invention, there may be mentioned the resins generally employed in the field of adhesives by those skilled in the art, such as modified polyterpene or terpene resins, hydrogenated rosin resins, polymerised rosin resins, rosin ester resins, hydrocarbon resins, mixtures of aromatic and aliphatic resins, etc. A synthetic resin formed of $C_5/C_9$ copolymers and marketed by GOOD YEAR under the name WINGTACK® 86 will be particularly preferred within the framework of the present invention.

Antioxidants are understood here as denoting the compounds commonly employed by those skilled in the art in order to ensure that the compounds used in the formulation of the hydrophilic adhesive mass, particularly the tackifying resins and the block copolymers, are stable towards oxygen, heat, ozone and ultraviolet radiation. It is possible to use one or more of these antioxidants in association.

Appropriate antioxidants which may thus be mentioned are phenolic antioxidants, such as, for example, the products marketed by CIBA GEIGY under the names IRGANOX® 1010, IRGANOX® 565 and IRGANOX® 1076, and sulphur-containing antioxidants, for example the zinc dibutyldithiocarbamate marketed by AKZO under the name PERKACIT® ZDBC.

The association of IRGANOX® 1010 and PERKACIT® ZDBC will be preferred within the framework of the present invention.

Hydrocolloid is understood here as denoting the compounds commonly used by those skilled in the art which are known for their ability to absorb hydrophilic liquids, particularly water, and transport them rapidly. Examples of appropriate hydrocolloids which may be mentioned are polyvinyl alcohol, gelatine, pectin, sodium alginates, natural vegetable gums such as carob gum, karaya gum, guar gum, gum arabic, etc., and cellulose derivatives such as hydroxyethyl celluloses, hydroxypropyl celluloses, carboxymethyl celluloses and their alkali metal salts such as the sodium or calcium salts. These hydrocolloids may be used by themselves or in association.

The alkali metal salts of carboxymethyl cellulose, particularly sodium carboxymethyl cellulose, will be preferred within the framework of the present invention.

Any type of plasticizer normally used by those skilled in the art for the preparation of adhesive mass based on styrene/olefin/styrene block copolymer can be used within the framework of the present invention, although it will be preferable to use plasticizing oils.

Plasticizing oils are understood here as denoting the mineral or vegetable oils commonly employed by those skilled in the art for plasticizing the block copolymers of the styrene/olefin/styrene type which are used in the composition of the adhesive mass.

The mineral oils generally used are mixtures of compounds of a paraffinic, naphthenic or aromatic nature in variable proportions.

Examples of plasticizing oils which may thus be mentioned are the products marketed by SHELL under the names ONDINA® and RISELLA® in the case of mixtures based on naphthenic and paraffinic compounds, or under the name CATENEX® in the case of mixtures based on naphthenic, aromatic and paraffinic compounds.

The mineral plasticizing oil marketed under the name CATENEX® N945 will be particularly preferred within the framework of the present invention.

The acrylate polymers suitable for carrying out the invention are pressure-sensitive acrylate compounds with a glass transition temperature (Tg) below $-20°$ C.

Such acrylate compounds are copolymers formed of:
  either at least one monomer selected from the group consisting of acrylic acid alkyl esters in which the linear or branched alkyl group of the ester contains 1 to 18 carbon atoms, preferably 4 to 10 carbon atoms and particularly 4 to 8 carbon atoms, for example methyl, ethyl, n-propyl, n-butyl, isobutyl, n-hexyl, 2-ethylhexyl, n-octyl, isooctyl, n-decyl and n-dodecyl acrylates, copolymerised with acrylic acid;
  or at least two monomers selected from the group consisting of acrylic acid alkyl esters in which the linear or branched alkyl group of the ester contains 1 to 18 carbon atoms, preferably 4 to 10 carbon atoms and particularly 4 to 8 carbon atoms, for example methyl, ethyl, n-propyl, n-butyl, isobutyl, n-hexyl, 2-ethylhexyl, n-octyl, isooctyl, n-decyl and n-dodecyl acrylates.

The respective percentages or proportions of these different monomers are adjusted to give a copolymer with the desired glass transition temperature, i.e. below $-20°$ C.

A copolymer containing at least one monomer selected from n-butyl acrylate, 2-ethylhexyl acrylate and isooctyl acrylate, copolymerised with acrylic acid, will preferably be used within the framework of the present invention.

Copolymers containing from 1 to 20% and preferably 1 to 10% by weight of acrylic acid, expressed relative to the total weight of all the monomers, will be very particularly preferred.

Such acrylate compounds can also be homopolymers whose constituent monomer is selected from the group consisting of acrylic acid alkyl esters in which the alkyl group of the ester is either a linear alkyl group containing 2 to 12 carbon atoms or an isobutyl, 2-ethylhexyl or isooctyl group.

Among these homopolymers, poly-n-butyl acrylate will be preferred within the framework of the present invention.

According to one particular characteristic of the invention, the products well known to those skilled in the art for their use in a solventless coating process, known as the hot melt process, will be chosen.

Examples which may thus be mentioned are the products marketed by BASF under the following names:

ACRONAL® A150F (n-butyl acrylate homopolymer with a glass transition temperature of −41° C.), ACRONAL® DS3435X (n-butyl acrylate homopolymer with a glass transition temperature of −46° C.), ACRONAL® DS3429 (n-butyl acrylate/2-ethylhexyl acrylate/acrylic acid copolymer with a glass transition temperature of −31° C.), and ACRONAL® DS3458 (n-butyl acrylate/acrylic acid copolymer with a glass transition temperature of −39° C.).

The product marketed by MONSANTO under the name:

MODAFLOW® (ethyl acrylate/2-ethylhexyl acrylate copolymer) may also be mentioned.

The hydrophilic adhesive mass according to the invention can be used in numerous applications for medical purposes. Thus there may be mentioned the production of bandages and dressings for the protection of the skin, for the protection of corns, calluses and soft corns, for the treatment of superficial dermoepidermal lesions, insect bites, exudative wounds, bedsores and burns, and for the treatment and prevention of blisters.

Numerous other applications are also possible, such as the production of adhesive joints employed in ostomy, orthopaedic devices for shock absorption in shoes, surgical sheets, adhesives for electrodes in the context of treatment of the human body with an electric current, and adhesives for fixing prostheses or devices to the skin or mucous membranes.

In the context of these applications, various products of a dermatological or therapeutic nature can be added to the formulation of the hydrophilic adhesive mass, examples being antifungals, antimicrobials, antibacterials such as sulfadiazine silver, pH regulators, healing accelerators, vitamins, trace elements, local anaesthetics, menthol, methyl salicylate, hormones, anti-inflammatories etc.

In the context of the production of a dressing for the treatment of blisters or the protection of wounds, burns and bedsores, the hydrophilic adhesive mass according to the invention is coated onto an appropriate support in the desired weight per unit area, according to the techniques known to those skilled in the art, by means of a solvent phase process or, preferably, by means of a hot melt process at a temperature generally of between 110 and 160° C.

The support is chosen as a function of the properties required (leaktightness, elasticity etc.), depending on the type of dressing and the intended application.

The support can take the form of a film made up of one or more layers with a thickness varying from 5 to 150 $\mu$m, or of a nonwoven or a foam with a thickness of 10 to 500 $\mu$m.

These supports based on synthetic or natural materials are those generally used by those skilled in the art in the field of dressings and the above-mentioned medical applications.

Thus there may be mentioned foams made of polyethylene, polyurethane or PVC, and nonwovens made of polypropylene, polyamide, polyester, ethyl cellulose, etc.

It will be preferable, however, to use films as supports, especially polyurethane films such as, for example, the products marketed by Smith and Nephew under the reference LASSO, or polyurethane films produced from the polyurethane marketed by B.F. GOODRICH under the name ESTANE®, low density polyethylene films such as, for example, those marketed by SOPAL, films based on thermoplastic polyether/polyester copolymer, such as, for example, the products marketed by DUPONT DE NEMOURS under the trademark Hytrel®, or composite films based on polyurethane and a nonwoven.

The dressings produced from the hydrophilic adhesive mass according to the invention can have any geometric shape, i.e. square, rectangular, circular or oval. Likewise, they can be of any size, which will be adapted according to the surface area of the part to be treated or protected.

In practical terms, the surface of the adhesive mass which is not bonded to the support may be covered with a protective layer or film to be peeled off before the dressing is used.

The whole formed in this way may itself be packaged in a leaktight protection, for example made of polyethylene/aluminium composites, or in blister packs.

By virtue of the specific nature of the composition of the formulations which can form the hydrophilic adhesive mass according to the invention, the latter has numerous advantages, which will now be explained.

It has in fact been found that, surprisingly, the addition, to the known adhesive masses of the prior art, of an acrylate polymer—a very viscous compound of an oleophilic nature which is poorly compatible or incompatible with hydrophilic liquids—makes it possible significantly to increase the absorption capacity of adhesive masses based on hydrocolloids. This unexpected phenomenon could be the result of a synergistic effect between the hydrocolloid and a degree of hydrophilicity imparted to the polymer by the polar character of the ester linkages of the acrylates. Now, in the context of the intended medical applications of the hydrophilic adhesive masses, the increase in absorption capacity is a decisive criterion.

It is actually impossible to achieve this result by increasing the amount of hydrocolloid indefinitely, because, beyond a certain value, the hydrocolloid degrades the adhesive properties of the mass and affects the physical properties, especially the cohesion, the deformability, the elasticity etc. There are also compatibility problems between the hydrophobic compounds, such as SIS copolymers, and hydrophilic compounds, such as the hydrocolloid, and it becomes impossible to obtain a homogeneous product of correct appearance. The addition of the acrylate polymer in a relatively small amount, compared with that of the elastomer/resin combination on the one hand and the hydrocolloid on the other, enables these problems to be avoided. It also makes it possible to achieve the difficult compromise between maximum absorption and acceptable adhesive and physical properties, which is essential for the desired medical applications.

This avoids or minimises the phenomena of loss or disintegration of a dressing after swelling and saturation with fluids in the context of the treatment of superficial exudative wounds and burns. The risks of maceration and irritation are reduced, so the dressing can be renewed painlessly and, in particular, less often.

This possibility of making the care easier and less frequent therefore affords better control over the treatment and the healing process.

Finally, despite the increase in its absorption capacity, the hydrophilic adhesive mass according to the invention retains its adhesiveness on the skin over time and even possess a greater adhesiveness than that of a conventional identical mass with no acrylate polymer added.

This makes it possible, for example, to produce a dressing for the treatment of blisters which adapts itself and sticks efficiently to the part to be protected, and whose absorption capacity makes it possible to prevent blistering and obtain an excellent hypoallergenic product.

Other advantages, characteristics and applications of the invention will be understood more clearly from the following description of Examples and comparative tests.

Of course, these data as a whole in no way imply a limitation but are given by way of illustration.

The following abbreviations have been used hereafter by way of convenience:
SIS: poly(styrene/isoprene) three-block copolymer.

EXAMPLE 1

14.2 kg of CATENEX® N945 (mineral oil marketed by SHELL), 19.8 kg of VECTOR® 4114 (SIS copolymer marketed by DEXCO), 0.4 kg of PERKACIT® ZDBC (zinc dibutyldithiocarbamate, antioxidant marketed by AKZO) and 0.4 kg of IRGANOX® 1010 (antioxidant marketed by CIBA-GEIGY) are introduced successively into a Z-blade mixer at a temperature of the order of 130° C. The mixture obtained is mixed at 130° C. for 35 minutes. 4.9 kg of ACRONAL® DS3458 (butyl acrylate/acrylic acid copolymer marketed by BASF) are then added and the mixture obtained is mixed for 10 minutes, still at 130° C. 30.2 kg of WINGTACK® 86 (tackifying resin marketed by GOOD YEAR) are then introduced and the mixture is mixed for a further 20 minutes, still at 130° C. Finally, 30 kg of BLANOSE® 7H4XF (sodium carboxymethyl cellulose marketed by AQUALON) are introduced and the mixture is mixed for a further 25 minutes. The resulting mixture is coated onto a film of siliconised paper at a rate of 600 g/m$^2$ at a temperature of between 120 and 150° C. The coating produced in this way is transferred to a 30 µm thick, polyurethane final support (produced from the polyurethane marketed by B.F. GOODRICH under the name ESTANE®). Shapes of the appropriate dimensions are then cut out and packaged in heat-sealing sachets or in blister packs.

EXAMPLE 2

The procedure is analogous to that of Example 1 except that in this case the product is coated onto the film of siliconised paper at a rate of 300 g/m$^2$.

EXAMPLE 3

The procedure is analogous to that of Example 1 except that a sodium carboxymethyl cellulose of different particle size distribution is used in this case. The 30 kg of BLANOSE® 7H4XF are therefore replaced here with the same amount of BLANOSE® 7H3XF (product also marketed by AQUALON).

EXAMPLE 4

The procedure is identical to that of Example 1 except that 14.8 kg of CATENEX® N945, 21.1 kg of VECTOR® 4114, 0.42 kg of PERKACIT® ZDBC, 0.42 kg of IRGANOX® 1010, 5 kg of ACRONAL® DS3458, 31.6 kg of WINGTACK® 86 and 26.6 kg of BLANOSE® 7H4XF are used in this case. The coating rate is still 600 g/m$^2$.

EXAMPLE 5

The procedure is identical to that of Example 1 except that a different SIS copolymer is employed in this case. 14.8 kg of CATENEX® N945, 21.1 kg of KRATON® D-1111CS (SIS copolymer marketed by SHELL Chemicals), 0.42 kg of PERKACIT® ZDBC, 0.42 kg of IRGANOX® 1010, 5.1 kg of ACRONAL® DS3458, 31.6 kg of WINGTACK® 86 and 26.6 kg of BLANOSE® 7H4XF are used here. This time the product is coated onto a film of siliconised paper at a rate of 1000 g/m$^2$ and the coating obtained is transferred to a 30 µm thick, polyurethane final support marketed by Smith and Nephew under the reference LASSO 687.

EXAMPLE 6

The procedure is analogous to that of Example 5 except that the acrylic acid ester homopolymer ACRONAL® A150F is employed in this case in place of the ACRONAL® DS3458. 14.2 kg of CATENEX® N945, 20.2 kg of KRATON® D-1111CS, 0.4 kg of PERKACIT® ZDBC, 0.4 kg of IRGANOX® 1010, 4.9 kg of ACRONAL® A150F (n-butyl acrylate marketed by BASF), 34.4 kg of WINGTACK® 86 and 26 kg of BLANOSE® 7H4XF are used here. This time the product is coated onto a film of siliconised paper at a rate of 600 g/m$^2$ and the coating obtained is transferred to a 30 µm thick, polyurethane final support (formed from ESTANE®) identical to that of Example 1.

EXAMPLE 7

The procedure is analogous to that of Example 5 except that the ACRONAL® DS3458 is replaced here with ACRONAL® DS3429, which is an n-butyl acrylate/2-ethylhexyl acrylate/acrylic acid copolymer marketed by BASF. 14.5 kg of CATENEX® N945, 20.6 kg of KRATON® D-1111CS, 0.41 kg of PERKACIT® ZDBC, 0.41 kg of IRGANOX® 1010, 3 kg of ACRONAL® DS3429, 35.1 kg of WINGTACK® 86 and 26 kg of BLANOSE® 7H4XF are used in this case. This time the product is coated onto a film of siliconised paper at a rate of 600 g/m$^2$ and the coating obtained is transferred to a 30 µm thick, low density polyethylene final support marketed by SOPAL.

EXAMPLE 8

The procedure is analogous to that of Example 7 except that 8% of ACRONAL® DS3429 are employed in this case instead of the 3% in Example 7, and the product is transferred to a polyether/polyester final support. 13.7 kg of CATENEX® N945, 19.6 kg of KRATON® D-1111CS, 0.39 kg of PERKACIT® ZDBC, 0.39 kg of IRGANOX® 1010, 8 kg of ACRONAL® DS3429, 33.3 kg of WINGTACK® 86 and 24.7 kg of BLANOSE® 7H4XF are therefore used here. The product is again coated onto a film of siliconised paper at a rate of 600 g/m$^2$, but this time the coating obtained is transferred to a 30 µm thick, final support formed of a thermoplastic polyether/polyester copolymer marketed by DUPONT DE NEMOURS under the name Hytrel®.

Comparative Example 1

15 kg of CATENEX® N945, 20.8 kg of VECTOR® 4114, 0.4 kg of PERKACIT® ZDBC and 0.4 kg of IRGANOX® 1010 are introduced successively into a Z-blade mixer at a temperature of the order of 130° C. The mixture obtained is mixed at 130° C. for 35 minutes. 31.8 kg of WINGTACK® 86 are then introduced and the mixture is mixed for a further 20 minutes, still at 130° C. Finally, 31.6 kg of BLANOSE® 7H4XF are added and the mixture is mixed for a further 25 minutes. The resulting mixture is coated onto a film of siliconised paper at a rate of 600 g/m$^2$ at a temperature of between 120 and 150° C. The coating produced in this way is transferred to a 30 µm thick, final support made of polyurethane (formed from ESTANE®), identical to that of Example 1. Shapes of the appropriate dimensions are then cut out and packaged in heat-sealing sachets or in blister packs.

Comparative Example 2

The procedure is analogous to that of Comparative Example 1 except that the coating rate in this case is 300 g/m$^2$.

Comparative Example 3

The procedure is analogous to that of Comparative Example 1 except that a sodium carboxymethyl cellulose of different particle size distribution is employed in this case. The BLANOSE® 7H4XF is replaced with the same amount of BLANOSE® 7H3XF. The coating rate is still 600 g/m² and the product is transferred to the same final support.

Comparative Example 4

The procedure is analogous to that of Comparative Example 1 except that 15.6 kg of CATENEX® N945, 22.2 kg of VECTOR® 4114, 0.44 kg of PERKACIT® ZDBC, 0.44 kg of IRGANOX® 1010, 33.3 kg of WINGTACK® 86 and 28 kg of BLANOSE® 7H4XF are used in this case.

Comparative Example 5

The procedure is analogous to that of Comparative Example 4 except that the VECTOR® 4114 is replaced with the same amount of KRATON® D-1111CS. This time, however, the product is coated onto a film of siliconised paper at a rate of 1000 g/m² and the resulting coating is transferred to a 30 μm thick, polyurethane final support marketed by Smith and Nephew under the reference LASSO 687.

Comparative Example 6

The procedure is analogous to that of Comparative Example 5 except that 14.9 kg of CATENEX® N945, 21.3 kg of KRATON® D-1111CS, 0.42 kg of PERKACIT® ZDBC, 0.42 kg of IRGANOX® 1010, 36.2 kg of WING-TACK® 86 and 26.8 kg of BLANOSE® 7H4XF are used in this case. The product is coated onto a film of siliconised paper at a rate of 600 g/m² and the resulting coating is transferred to a polyurethane final support identical to that of Example 1.

Comparative Example 7

The procedure is analogous to that of Comparative Example 5 except that in this case the coating obtained is transferred to a 30 μm thick, low density polyethylene final support marketed by SOPAL.

Comparative Example 8

The procedure is analogous to that of Comparative Example 5 except that in this case the coating obtained is transferred to a 30 μm thick, final support formed of a thermoplastic polyether/polyester copolymer marketed by DUPONT DE NEMOURS under the name HYTREL®.

Tests

In order to demonstrate the absorption capacity of the hydrophilic adhesive masses according to the invention, absorption measurements were made on different samples obtained from Examples 1 to 8.

For comparison purposes, the same procedure was applied to determination of the absorption of hydrophilic adhesive masses which were identical except that no acrylate polymer was incorporated (Comparative Examples CE1 to CE8).

These measurements were made according to the following protocol:

The sample used is a sample produced as described in Examples 1 to 8 and Comparative Examples 1 to 8, formed of the final support, the hydrophilic adhesive mass and the film of siliconised paper serving as a peel-off protector, which is cut to produce an adhesive tape.

The measurement is effected by the difference in the weight of the adhesive tape before and after it has been brought into contact for a fixed period of time—in this case 24 hours—with a cylinder filled with a reference liquid.

In the following tests, the reference liquid is a solution of Dextran D4876 (marketed by Sigma) containing 60 g per litre in 0.15 molar sodium chloride solution.

The measurements are made according to the following steps:

A sample (of 16 cm², for example, in this case) of the adhesive tape to be tested is cut out and the protective film is removed.

A Teflon cylinder is placed at the centre of the part to be tested and a slight pressure is exerted so that it adheres correctly to the adhesive tape.

The resulting assembly is weighed; let $P_0$ be the weight obtained.

10 ml of the preprepared reference liquid are then introduced into the cylinder.

The assembly is then left in contact with the liquid at 23° C. for 24 hours.

When the 24 hours have elapsed, the cylinder/adhesive tape assembly is weighed after the unabsorbed solution has been removed; let $P_1$ be the weight obtained.

The absorption capacity, corresponding to the surface absorption, is calculated using the following formula:

absorption=$4(P_1-P_0)/\pi D^2$, where D is the diameter of the cylinder, i.e. 0.027 m in this case.

Hence the absorption, expressed in g/m², is defined here by:

$$\text{absorption}=(P_1-P_0)10^4/5.73$$

Each test is performed at least 5 times.

The absorption capacity obtained is the mean of these different tests.

The results obtained have been collated in Table I.

TABLE I

| | ABSORPTION TESTS | | | | | | | | | | | | | | | |
|---|---|---|---|---|---|---|---|---|---|---|---|---|---|---|---|---|
| | EX1 | CE1 | EX2 | CE2 | EX3 | CE3 | EX4 | CE4 | EX5 | CE5 | EX6 | CE6 | EX7 | CE7 | EX8 | CE8 |
| A | 2990 | 530 | 2330 | 470 | 2820 | 1450 | 1370 | 250 | 1585 | 625 | 1000 | 490 | 980 | 300 | 640 | 250 |
| R | 5.6 | | 5 | | 1.95 | | 5.5 | | 2.5 | | 2 | | 3.3 | | 2.5 | |

TABLE I-continued

ABSORPTION TESTS

|  | EX1 | CE1 | EX2 | CE2 | EX3 | CE3 | EX4 | CE4 | EX5 | CE5 | EX6 | CE6 | EX7 | CE7 | EX8 | CE8 |
|---|---|---|---|---|---|---|---|---|---|---|---|---|---|---|---|---|
| Support | PU ESTANE ® | | PU ESTANE ® | | PU ESTANE ® | | PU ESTANE ® | | PU S + N | | PU ESTANE ® | | PE SOPAL | | HYTREL ® | |
| G | 600 | | 300 | | 600 | | 600 | | 1000 | | 600 | | 600 | | 600 | |

A: represents the absorption expressed in g/m².
R: represents the ratio of the absorption of the Examples (EX) of hydrophilic adhesive masses according to the invention to that of the Comparative Examples (CE) of identical masses without acrylate polymer.
G: represents the weight per unit area of the adhesive tapes used to measure the absorption expressed in g/m².
Support: represents the nature of the support to which the hydrophilic adhesive mass is applied:
polyurethane film formed from the polyurethane ESTANE ®:PU ESTANE ®
HYTREL ® polyether/polyester film
polyethylene film marketed by SOPAL: PE SOPAL
polyurethane film marketed by Smith and Nephew: PU S + N Analysis of the results collated in Table I give a perfect illustration of the favourable influence of the addition of acrylate polymer on the increase in absorption capacity of the hydrophilic adhesive masses according to the invention. The ratio R shows that the absorption capacity of the adhesive masses according to the invention is always markedly greater than that of the Comparative Examples, being up to 5.6 times greater in the best case.

Thus the absorption capacity is:

5.6 times greater for Example 1 than for Comparative Example CE 1, 5 times greater for Example 2 than for Comparative Example CE2, 2 times greater for Example 3 than for Comparative Example CE3, 5.5 times greater for Example 4 than for Comparative Example CE4, 2.5 times greater for Example 5 than for Comparative Example CE5, 2 times greater for Example 6 than for Comparative Example CE6, 3.3 times greater for Example 7 than for Comparative Example CE7, and 2.5 times greater for Example 8 than for Comparative Example CE8.

It is also seen that this increase is found for all the weights tested, i.e. 1000, 600 and 300 g/m².

Thus the ratio R is virtually identical for Examples 1 and 2, being 5.6 and 5 respectively.

It is also found that, irrespective of the nature of the supports used and hence their permeability, an increase in the absorption capacity is always found. This is perfectly illustrated by Examples 7 and 8 and even Example 5.

Likewise, irrespective of the nature and percentage of the acrylate polymer used (5% of ACRONAL® 3458 in Examples 1 to 5; 5% of ACRONAL® A150F in Example 6; and 3 and 8% of ACRONAL® 3429 in Examples 7 and 8 respectively), a significant increase in the absorption capacity is always found, being at least doubled.

Finally, even if one varies the nature of the sodium carboxymethyl cellulose (different particle size distribution in Example 3) or the nature of the poly(SIS) polymers in the composition (KRATON® D1111CS for Examples 5 to 8 and VECTOR® 4114 for Examples 1 to 4), or even their proportions, the increase in absorption capacity is always preserved.

In conclusion, all these findings and these results undeniably demonstrate that, in terms of the composition of the hydrophilic adhesive mass, there is a relatively large amount of room for manoeuvre, despite the introduction of an additional compound, namely the acrylate polymer, in making a product which possesses a markedly improved absorption capacity. This is a particularly important advantage for the production of protective dressings and dressings for the treatment of blisters, superficial dermo-epidermal lesions, wounds and burns, in which these hydrophilic adhesive masses are used.

We claim:

1. Hydrophilic adhesive mass for medical purposes which comprises:

(a) 10 to 35 parts by weight of a poly (styrene/olefin/styrene) block copolymer, (b) 20 to 50 parts by weight of a tackifying resin, (c) 2 to 15 parts by weight of an acrylate polymer with a glass transition temperature below −20° C., (d) 2 to 25 parts by weight of a plasticizer, (e) 20 to 50 parts by weight of a hydrocolloid, and (f) 0.1 to 2 parts by weight of at least one antioxidant.

2. Hydrophilic adhesive mass of claim 1, wherein said poly(styrene/olefin/styrene) block copolymer is poly(styrene/isoprene/styrene).

3. Hydrophilic adhesive mass of claim 1, wherein the acrylate polymer with a glass transition temperature below −20° C. is a copolymer formed from at least one monomer selected from the group consisting of acrylic acid alkyl esters in which the linear or branched alkyl group of the ester contains 1 to 18 carbon atoms, copolymerized with acrylic acid.

4. Hydrophilic adhesive mass of claim 1, wherein the acrylate polymer with a glass transition temperature below −20° C. is a copolymer formed from at least one monomer selected from the group consisting of acrylic acid alkyl esters in which the linear or branched alkyl group of the ester contains 4 to 10 carbon atoms, copolymerised with acrylic acid.

5. Hydrophilic adhesive mass of claim 1, wherein the acrylate polymer with a glass transition temperature below −20° C. is a copolymer formed from at least one monomer selected from the group consisting of methyl, ethyl, n-propyl, n-butyl, isobutyl, n-hexyl, 2-ethylhexyl, n-octyl, isooctyl, n-decyl and n-dodecyl acrylates, copolymerized with acrylic acid.

6. Hydrophilic adhesive mass of claim 1, wherein the above-mentioned acrylate copolymer is a copolymer formed from at least one monomer selected from the group consisting of n-butyl acrylate, 2-ethylhexyl acrylate and isooctyl acrylate, copolymerized with acrylic acid.

7. Hydrophilic adhesive mass of claim 6, wherein the acrylate polymer is a copolymer selected from the group consisting of an n-butyl acrylate/acrylic acid copolymer with a glass transition temperature of −39° C., and an n-butyl acrylate/2-ethylhexyl acrylate/acrylic acid copolymer with a glass transition temperature of −31° C.

8. Hydrophilic adhesive mass of claim 6, wherein the acrylate copolymer comprises from 1 to 20% acrylic acid, relative to total monomer weight.

9. Hydrophilic adhesive mass of claim 6, wherein the copolymer comprises from 1 to 10% by weight of acrylic acid, relative to total monomer weight.

10. Hydrophilic adhesive mass of claim 1, wherein the acrylate polymer with a glass transition temperature below −20° C. is a copolymer formed from at least two monomers selected from the group consisting of acrylic acid alkyl esters in which the linear or branched alkyl group of the ester contains 1 to 18 carbon atoms.

11. Hydrophilic adhesive mass of claim 1, wherein the acrylate polymer with a glass transition temperature below −20° C. is a copolymer formed from at least two monomers selected from the group consisting of acrylic acid alkyl esters in which the linear or branched alkyl group of the ester contains 4 to 10 carbon atoms.

12. Hydrophilic adhesive mass of claim 1, wherein the acrylate polymer with a glass transition temperature below −20° C. is a copolymer formed from at least two monomers selected from the group consisting of methyl, ethyl, n-propyl, n-butyl, isobutyl, n-hexyl, 2-ethylhexyl, n-octyl, isooctyl, n-decyl and n-dodecyl acrylates.

13. Hydrophilic adhesive mass of claim 1, wherein said acrylate polymer with a glass transition temperature below −20° C. is a homopolymer whose constituent monomer is selected from the group consisting of acrylic acid alkyl esters in which the alkyl group of the ester is selected from the group consisting of a linear alkyl group containing 2 to 12 carbon atoms, an isobutyl group, a 2-ethylhexyl group and an isooctyl group.

14. Hydrophilic adhesive mass of claim 13, wherein said acrylate polymer is an n-butyl acrylate homopolymer with a glass transition temperature of −41° C.

15. Hydrophilic adhesive mass of claim 1, wherein the above-mentioned block copolymer is a poly (styrene/isoprene/styrene) with a styrene content of between 14 and 52% by weight.

16. Hydrophilic adhesive mass of claim 15, wherein the above-mentioned block copolymer is a poly (styrene/isoprene/styrene) with a styrene content of between 14 and 30% by weight.

17. Hydrophilic adhesive mass of claim 1, wherein the hydrocolloid is an alkali metal salt of carboxymethyl cellulose.

18. Hydrophilic adhesive mass of claim 17, wherein the hydrocolloid is sodium carboxymethyl cellulose.

19. Hydrophilic adhesive mass of claim 1, wherein the plasticizer is a mineral plasticizing oil.

20. Hydrophilic adhesive mass of claim 19, wherein the mineral plasticizing oil is an oil selected from the group consisting of naphthenic, paraffinic and aromatic compounds.

21. Hydrophilic adhesive mass of claim 1, which comprises, for a total of 100 parts by weight:

18 to 22 parts by weight of a poly (styrene/isoprene/styrene) three-block copolymer, 25 to 35 parts by weight of a tackifying resin, 3 to 8 parts by weight of an n-butyl acrylate/acrylic acid copolymer with a glass transition temperature of −39° C., 10 to 20 parts by weight of a mineral plasticizing oil, 25 to 35 parts by weight of sodium carboxymethyl cellulose, 0.3 to 0.8 part by weight of a phenolic antioxidant, and 0.3 to 0.8 part by weight of sulfur-containing antioxidant zinc dibutyldithiocarbamate.

22. Hydrophilic adhesive mass of claim 1, which comprises, for a total of 100 parts by weight:

19.8 parts by weight of a poly(styrene/isoprene/styrene) three-block copolymer, 30.2 parts by weight of a tackifying resin, 4.9 parts by weight of an n-butyl acrylate/acrylic acid copolymer with a glass transition temperature of −39° C., 14.3 parts by weight of a mineral plasticizing oil, 30 parts by weight of sodium carboxymethyl cellulose, 0.4 part by weight of a phenolic antioxidant, and 0.4 part by weight of sulfur-containing antioxidant zinc dibutyldithiocarbamate.

23. Hydrophilic adhesive mass of claim 15, which comprises, for a total of 100 parts by weight:

18 to 22 parts by weight of a poly (styrene/isoprene/styrene) three-block copolymer, 25 to 35 parts by weight of a tackifying resin, 3 to 8 parts by weight of an n-butyl acrylate/acrylic acid copolymer with a glass transition temperature of −39° C., 10 to 20 parts by weight of a mineral plasticizing oil, 25 to 35 parts by weight of sodium carboxymethyl cellulose, 0.3 to 0.8 part by weight of a phenolic antioxidant, and 0.3 to 0.8 part by weight of sulfur-containing antioxidant zinc dibutyldithiocarbamate.

24. Hydrophilic adhesive mass of claim 15, which comprises, for a total of 100 parts by weight:

19.8 parts by weight of a poly (styrene/isoprene/styrene) three-block copolymer, 30.2 parts by weight of a tackifying resin, 4.9 parts by weight of an n-butyl acrylate/acrylic acid copolymer with a glass transition temperature of −39° C., 14.3 parts by weight of a mineral plasticizing oil, 30 parts by weight of sodium carboxymethyl cellulose, 0.4 part by weight of a phenolic antioxidant, and 0.4 part by weight of sulfur-containing antioxidant zinc dibutyldithiocarbamate.

25. A dressing for the treatment of blisters, superficial dermo-epidermal lesions of the skin, exudative wounds and burns, which dressing comprises a support onto which a hydrophilic adhesive mass according to claim 1 is coated.

* * * * *